(12) United States Patent
Stoffel

(10) Patent No.: US 11,690,506 B2
(45) Date of Patent: Jul. 4, 2023

(54) VIDEO LARYNGOSCOPE APPARATUS

(71) Applicant: Pavisus AS, Oslo (NO)

(72) Inventor: Daniel Stoffel, Rykkinn (NO)

(73) Assignee: PAVISUS AS, Oslo (NO)

( * ) Notice: Subject to any disclaimer, the term of this patent is extended or adjusted under 35 U.S.C. 154(b) by 144 days.

(21) Appl. No.: 17/181,649

(22) Filed: Feb. 22, 2021

(65) Prior Publication Data
US 2022/0000334 A1    Jan. 6, 2022

(30) Foreign Application Priority Data

Jul. 6, 2020  (NO) .................................. 20200789
Jul. 6, 2020  (NO) .................................. 20200790

(51) Int. Cl.
*A61B 1/267* (2006.01)
*A61B 1/00* (2006.01)
(Continued)

(52) U.S. Cl.
CPC ............ *A61B 1/267* (2013.01); *A61B 1/0005* (2013.01); *A61B 1/00016* (2013.01);
(Continued)

(58) Field of Classification Search
USPC ......................................................... 600/190
See application file for complete search history.

(56) References Cited

U.S. PATENT DOCUMENTS 2,630,114 A * 3/1953 Hart ........................ A61B 1/267
                                                      403/103
7,824,331 B1 * 11/2010 Granton ............... A61B 1/0008
                                                      600/190
(Continued)

FOREIGN PATENT DOCUMENTS

| CN | 20973394 U | 12/2019 |
|----|------------|---------|
| EP | 2944249 A1 | 11/2015 |
| GB | 2481515 A | 12/2011 |
| WO | WO 2008/157170 A2 | 12/2008 |

(Continued)

OTHER PUBLICATIONS

International Search Report and Written Opinion of the International Searching Authority directed to related International Patent Application No. PCT/IB2021/055967, dated Nov. 18, 2021; 18 pages.

*Primary Examiner* — Michael J Carey
*Assistant Examiner* — Minqiao Huang
(74) *Attorney, Agent, or Firm* — Sterne, Kessler, Goldstein & Fox P.L.L.C.

(57) ABSTRACT

Described herein is a video laryngoscope apparatus for inspection of an oral cavity region of a patient is disclosed. The video laryngoscope includes an apparatus body, a camera arm unit configured to receive and releasably attach thereto a disposable laryngoscope blade, a light source coupled to the camera arm unit, a communication unit, and a power source. The apparatus body includes a proximal end and a distal end, and the apparatus body is elongate and configured to be hand-held by an operator of the video laryngoscope. The camera arm unit includes a proximal end and a distal end with a camera, and the proximal end of the camera arm unit is connected to the distal end of the apparatus body utilizing an adjustable rotary position linkage member. The communication unit is connected via a linkage device to the proximal end of the apparatus body, and the power source is housed by the apparatus body.

27 Claims, 16 Drawing Sheets

(51) Int. Cl.
*A61B 1/05* (2006.01)
*A61B 1/06* (2006.01)
*A61B 1/015* (2006.01)
*A61M 16/01* (2006.01)

(52) U.S. Cl.
CPC ...... *A61B 1/00101* (2013.01); *A61B 1/00103* (2013.01); *A61B 1/015* (2013.01); *A61B 1/05* (2013.01); *A61B 1/0676* (2013.01); *A61B 1/0684* (2013.01); *A61M 16/01* (2013.01)

(56) References Cited

U.S. PATENT DOCUMENTS

| | | | | |
|---|---|---|---|---|
| 8,083,672 | B2 * | 12/2011 | Minson | A61B 1/267 600/190 |
| 8,414,481 | B2 * | 4/2013 | Hakanen | A61B 1/06 600/196 |
| 8,998,805 | B2 * | 4/2015 | Takeda | A61B 1/267 600/188 |
| 9,090,277 | B1 * | 7/2015 | Chen | B62B 9/245 |
| 9,588,478 | B1 * | 3/2017 | Fan | G03G 21/1676 |
| 10,995,842 | B1 * | 5/2021 | Siemer, Jr. | F16H 55/52 |
| 2010/0101569 | A1 * | 4/2010 | Kim | A61B 1/267 128/203.12 |
| 2010/0261967 | A1 * | 10/2010 | Pacey | A61B 1/00142 600/188 |
| 2011/0028790 | A1 * | 2/2011 | Farr | A61B 90/20 600/187 |
| 2012/0071725 | A1 * | 3/2012 | Plevnik | A61B 1/00052 600/188 |
| 2014/0296645 | A1 * | 10/2014 | McGrath | A61B 1/00101 600/196 |
| 2015/0099934 | A1 | 4/2015 | Sartore | |
| 2016/0022132 | A1 * | 1/2016 | Chan | A61B 1/04 600/188 |
| 2017/0044807 | A1 * | 2/2017 | Clark | E05F 17/00 |
| 2017/0105614 | A1 | 4/2017 | McWilliam et al. | |
| 2017/0215720 | A1 * | 8/2017 | Walker | A61B 1/0002 |
| 2018/0168433 | A1 * | 6/2018 | Meyer | A61B 1/00016 |
| 2019/0133430 | A1 * | 5/2019 | Inglis | A61B 1/00016 |
| 2019/0142262 | A1 * | 5/2019 | Inglis | A61B 1/0005 600/188 |
| 2020/0337546 | A1 * | 10/2020 | Huang | A61B 1/267 |
| 2021/0219834 | A1 * | 7/2021 | Velez Rivera | A61B 1/00128 |
| 2022/0000354 | A1 | 1/2022 | Stoffel | |

FOREIGN PATENT DOCUMENTS

| | | |
|---|---|---|
| WO | WO 2019/032400 A1 | 2/2019 |
| WO | WO 2019/197868 A1 | 10/2019 |

* cited by examiner

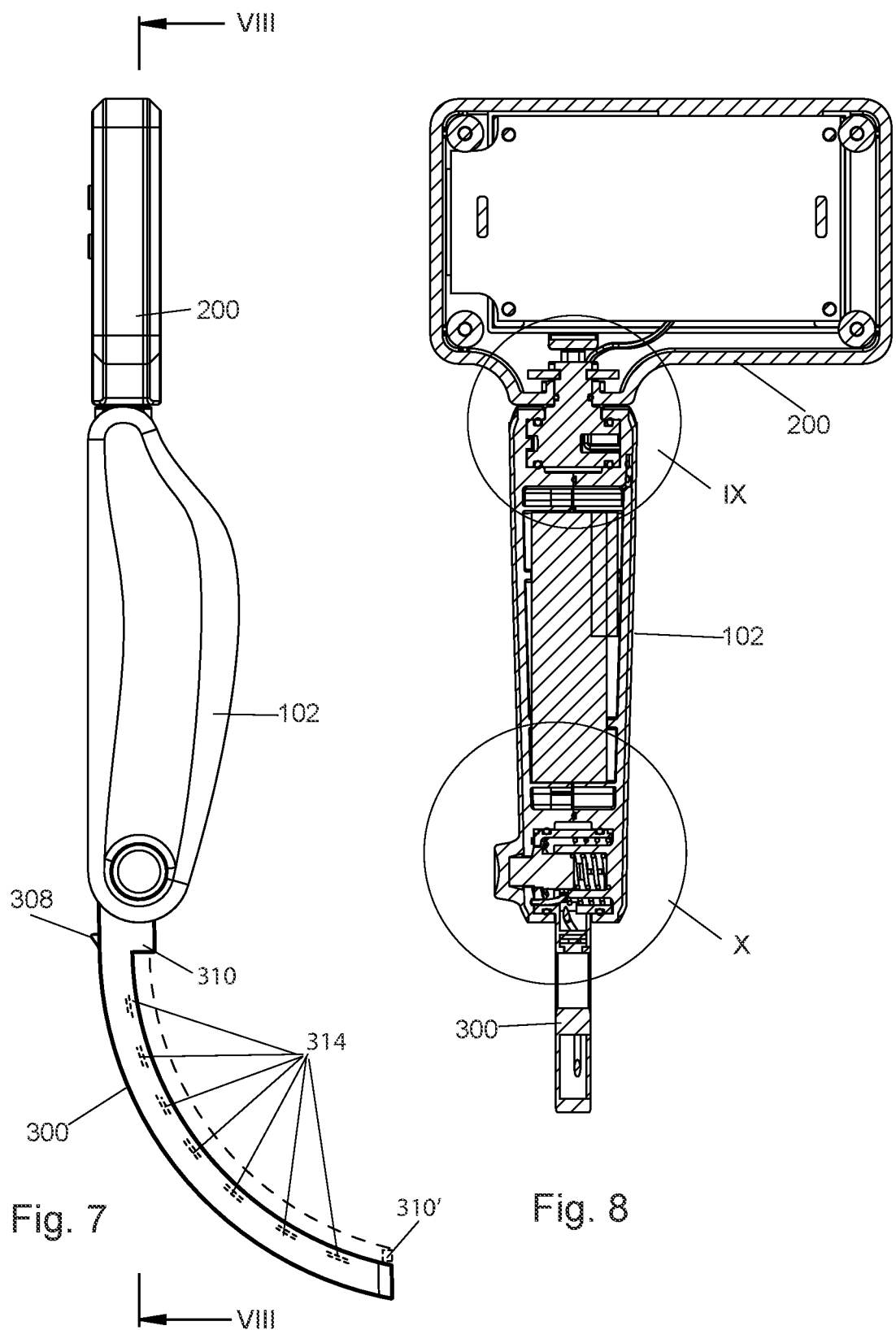

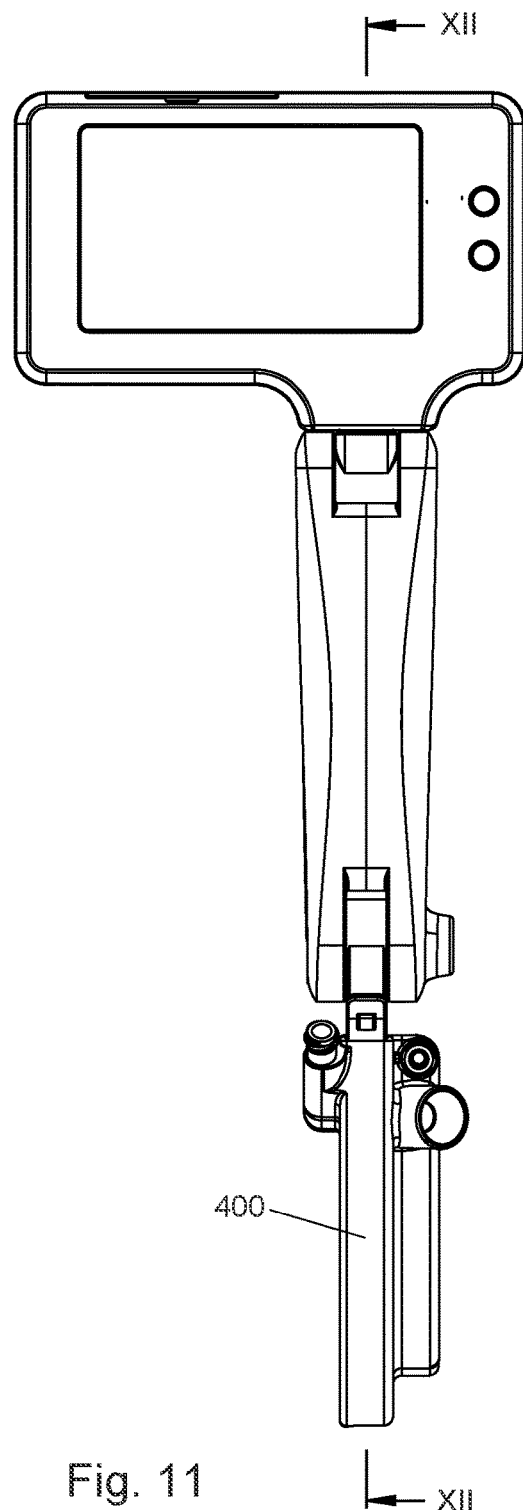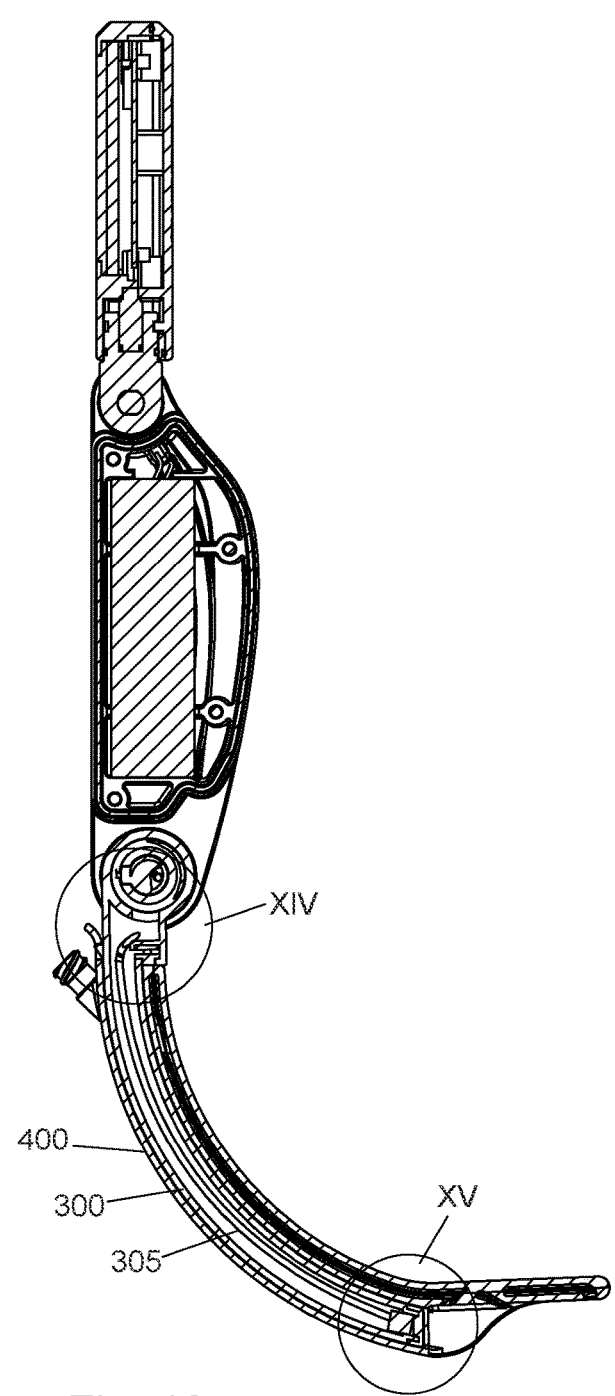
Fig. 11
Fig. 12

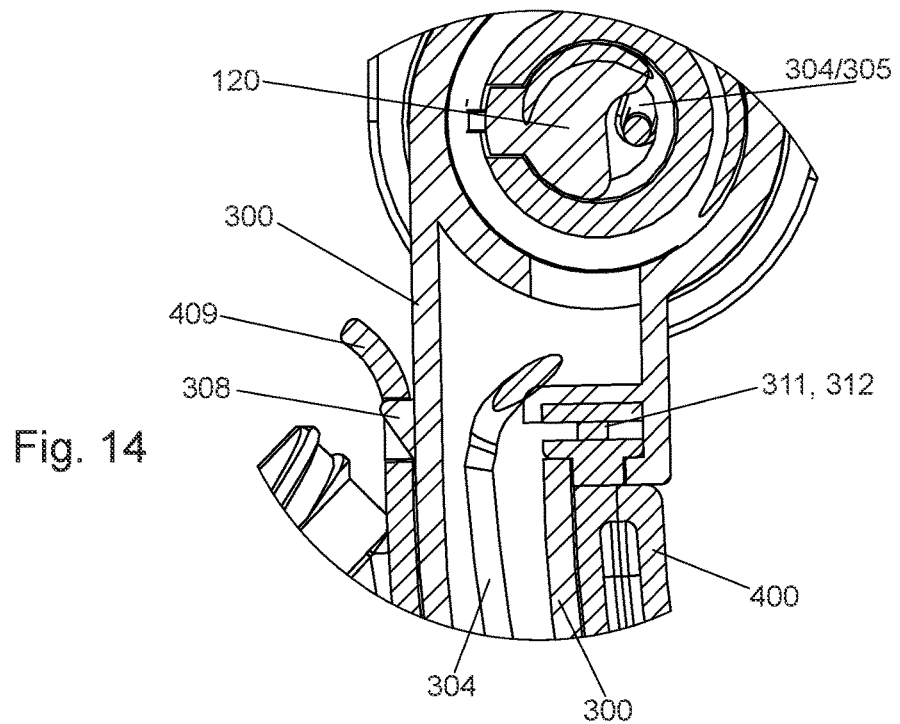
Fig. 14
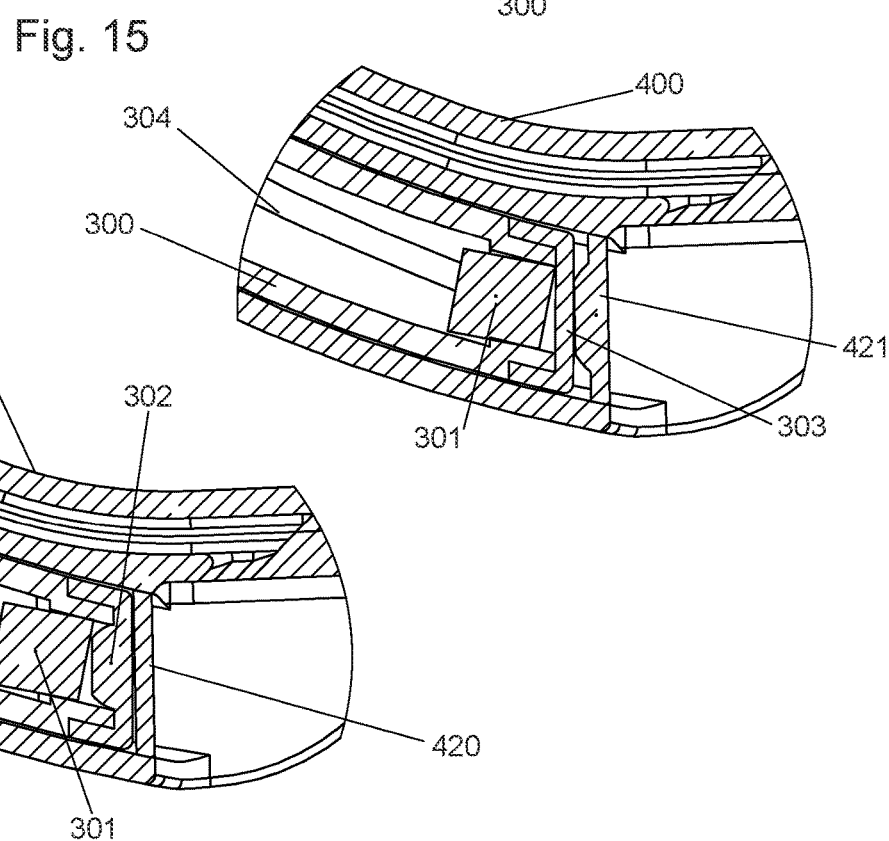
Fig. 15
Fig. 16

VIDEO LARYNGOSCOPE APPARATUS

CROSS-REFERENCE TO RELATED APPLICATIONS

This application claims priority to Norwegian App. No. 20200790 filed on Jul. 6, 2020 and Norwegian App. No. 20200789 filed on Jul. 6, 2020, the disclosures of which are incorporated by reference herein in their entireties. This application is related to co-pending U.S. patent application Ser. No. 17/181,640 by Daniel Stoffel, entitled "Disposable Laryngoscope Blade," filed on even date herewith, the disclosure of which is incorporated by reference herein in its entirety

BACKGROUND

Field

Embodiments of the application relate to a medical instrument and more particularly an instrument for performing a medical procedure in the field of anaesthesiology where a breathing tube is placed into the patient's trachea or for performing medical visual examinations of the respiratory tract.

Background

Video laryngoscopes are used to assist personnel performing tracheal intubations in patients. A video laryngoscope apparatus may include a handheld portion, a screen unit, and a laryngoscope blade for insertion into a patient's oral cavity for tracheal intubation of a patient. Intubation may be performed when a patient's airway is obstructed or when a patient is in a depressed state of consciousness, in a coma, or not breathing, as a result of an accident, a medically-induced coma, or another situation causing physical dysfunction. In some cases, intubation may be performed in a hospital by specially trained personnel, anesthetists, or anesthetic nurses, or outside of a hospital by less trained personnel.

As intubation may most often be performed in critical situations, there may be a need for video laryngoscopy devices that are made for easy mobility and use in and out of hospitals, such as in operation rooms, emergency departments, humanitarian healthcare organizations, in military, and in environments such as ambulances, helicopters, planes or in the battlefield. There may also be a need to provide assistance from experts who are remotely located to less trained personnel performing intubations on patients, such as in military and civilian settings for use in ambulances, helicopters, airplanes, in the field, and in other medical situations outside the hospital and operation rooms.

Video laryngoscopes may also provide user feedback that increases the chances of success of the intubation procedure. Current medical device manufacturers offer handheld video laryngoscope apparatuses with laryngoscope blades with a camera for providing a visual presentation of a patient's throat anatomy on a screen for assisting personnel during an intubation process of a patient. Conventionally, a video laryngoscope has a camera arm onto which the laryngoscope blade is releasably attached, and the angle between the laryngoscope handle and the camera arm may be permanently fixed. This current configuration of the video laryngoscope may make it difficult for an individual to insert the video laryngoscope into the oral cavity of a patient when the patient's head is in an inconvenient posture or position. In some cases, the laryngoscope's configuration might not be optimal for operation, and a display unit that is attached to the laryngoscope's handle may subsequently end up at a location that renders visual observation thereof by the individual performing the intubation cumbersome.

Furthermore, video laryngoscopes may necessitate more stringent cleaning procedures compared to traditional laryngoscopes, due to their more complex shape, structure and functionality.

BRIEF SUMMARY

Accordingly, there may be a need for improved laryngoscope devices that are hygienic, easy and simple to operate, and configured to provide direct feedback to the individual performing intubation on a patient (e.g., medically trained personnel or less experienced personnel), which may be a matter of life or death for the patient.

The present disclosure provides a video laryngoscope apparatus with a detachable and disposable blade that simplifies cleaning of the video laryngoscope, yet incorporates all the medical functions needed by enabling video vision, injection of local anesthetics, and oxygen, and removal of any bodily fluids that may block the airway. To simplify the need for cleaning the laryngoscope apparatus and minimizing the risk of transmitting diseases, disposable single-use blades may be utilized to protect the patient by covering the camera arm of the laryngoscope upon insertion into the oral cavity of the patient.

According to a first aspect of the disclosure, there is provided a video laryngoscope for inspection of an oral cavity region of a patient, comprising an elongate apparatus body configured to be hand-held, a laryngoscope camera arm unit with a camera, a light source, a laryngoscope blade releasably attachable onto the camera arm unit, a communication unit connected via a linkage device to a proximal end of said body, and a power source. The camera arm at its proximal end connects with a distal end of the apparatus body utilizing an adjustable rotary position linkage member.

The proximal end of the apparatus body is defined as the upper end. The communication unit is suitably provided with a screen. The linkage device is for positioning the communication unit at different angles relative to the apparatus body. The laryngoscope camera arm unit serves as a blade arm support and the associated blade is releasably attachable to the camera arm at a proximal end thereof, enabling folding of the blade along the apparatus body (or handgrip) and providing selectable angular positions outward relative to the apparatus body.

The camera arm (blade arm) unit comprises a video camera at its distal end position, and a lens is located in front of the camera. The camera arm unit is shaped to retain a laryngoscope blade with a specially made channel or slot to engage with the camera arm unit.

The rotary position linkage member connecting the camera arm to the apparatus body comprises a spring and clutch assembly with a force detection unit and means for angle detection. The apparatus body is shaped for easy grip by one hand. There is a release and lock button for control of the camera arm and blade by the position linkage member, accessible for operation by finger on the hand holding the body or any other finger.

The camera arm unit, which comprises a video camera and lens at its distal end, has a light source as defined and shown. The blade contains illumination enhancing means for proper illumination of the oral cavity of the patient. The blade is made to be removable and of a disposable type.

In a second aspect of the disclosure, there is provided a video laryngoscope for use on a patient, the laryngoscope comprising a camera arm with video camera and a laryngoscope blade releasably attachable onto the camera arm. The laryngoscope blade exhibits a tubular portion configured to releasably fit onto and enclose the camera arm, and another portion which internally incorporates at least two fluidic channels extending in the longitudinal direction of the blade, said channels each having at least two openings, at least one channel opening being at a proximal end of the blade and at least one further channel opening being at one of: a distal end location of the blade and location between the proximal and distal ends of the blade.

The blade has enclosed channels for transport of fluids, such as oxygen, local anesthetics and for cleansing of the camera lens or view window, and with a separate enclosed channel for suction of bodily fluids from the patient. There are fluid flow connectors with valve function on the blade for the tubes for in-flow transport of fluids, e.g. gas. Further, at the proximal region of the blade, there is a suction outlet connector for fluids that have been sucked and/or collected from the patient. This provides the medical personnel with valuable time to organize and perform critical life aid and deliver oxygen to be blown directly onto the opening of the trachea of the patient, which may be critically important in case of a patient having low oxygen level in the blood due to lung function issues.

The laryngoscope apparatus includes sensors measuring force, angles and software images and other related medical information, which are directed to the user, and the laryngoscope will record any operation for later studies. Information and images are shown on the display. The laryngoscope communication unit is either voice-operated or by touch screen, alternatively by key function buttons and has means for remote communication and sharing of data with other resources such as databases (medical), or other special personnel remote from the site of operation.

In an embodiment, a video laryngoscope apparatus for inspection of an oral cavity region of a patient is disclosed. The video laryngoscope apparatus includes an apparatus body, a camera arm unit, a light source coupled to the camera arm unit, a communication unit, and a power source. The apparatus body includes a proximal end and a distal end, in which the apparatus body is elongate and configured to be hand-held by an operator of the video laryngoscope. The camera arm unit includes a proximal end and a distal end with a camera, and the proximal end of the camera arm unit is connected to the distal end of the apparatus body utilizing a rotary position linkage member that is adjustable. The camera arm unit is configured to receive and releasably attach thereto a disposable laryngoscope blade. The communication unit is connected via a linkage device to the proximal end of the apparatus body, and the power source is housed by the apparatus body.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

FIG. 7 is a diagram showing a side view of the laryngoscope, including LED unit along the camera arm, according to embodiments of the present disclosure.

FIG. 8 is a diagram showing section VIII-VIII of the laryngoscope of FIG. 7, according to embodiments of the present disclosure.

FIG. 11 is a diagram showing an example laryngoscope with a blade fixed onto the camera arm of the laryngoscope, according to embodiments of the present disclosure.

FIG. 12 is a diagram showing section XII-XII of the laryngoscope of FIG. 11, according to embodiments of the present disclosure.

FIG. 14 is a diagram showing an enlarged view of region XIV of the laryngoscope shown in FIGS. 12 and 13, according to embodiments of the present disclosure.

FIG. 15 is a diagram showing an enlarged view of region XV of the laryngoscope shown in FIGS. 12 and 13, according to embodiments of the present disclosure.

FIG. 16 is a diagram showing a modification of FIG. 15 with a transparent window in front of the camera instead of a lens, according to embodiments of the present disclosure.

Figure 1:
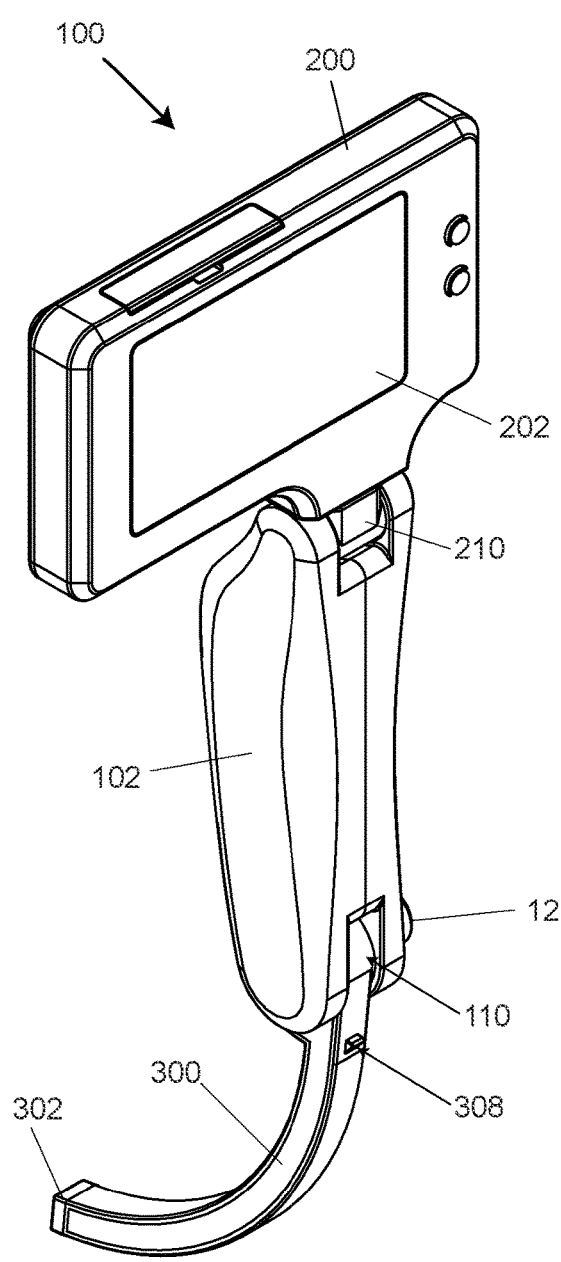
FIG. 1 is a diagram of a perspective view of an example video laryngoscope with a handgrip, a communication unit, and a camera arm unit for retaining a laryngoscope blade, according to embodiments of the present disclosure.
Figure 2:
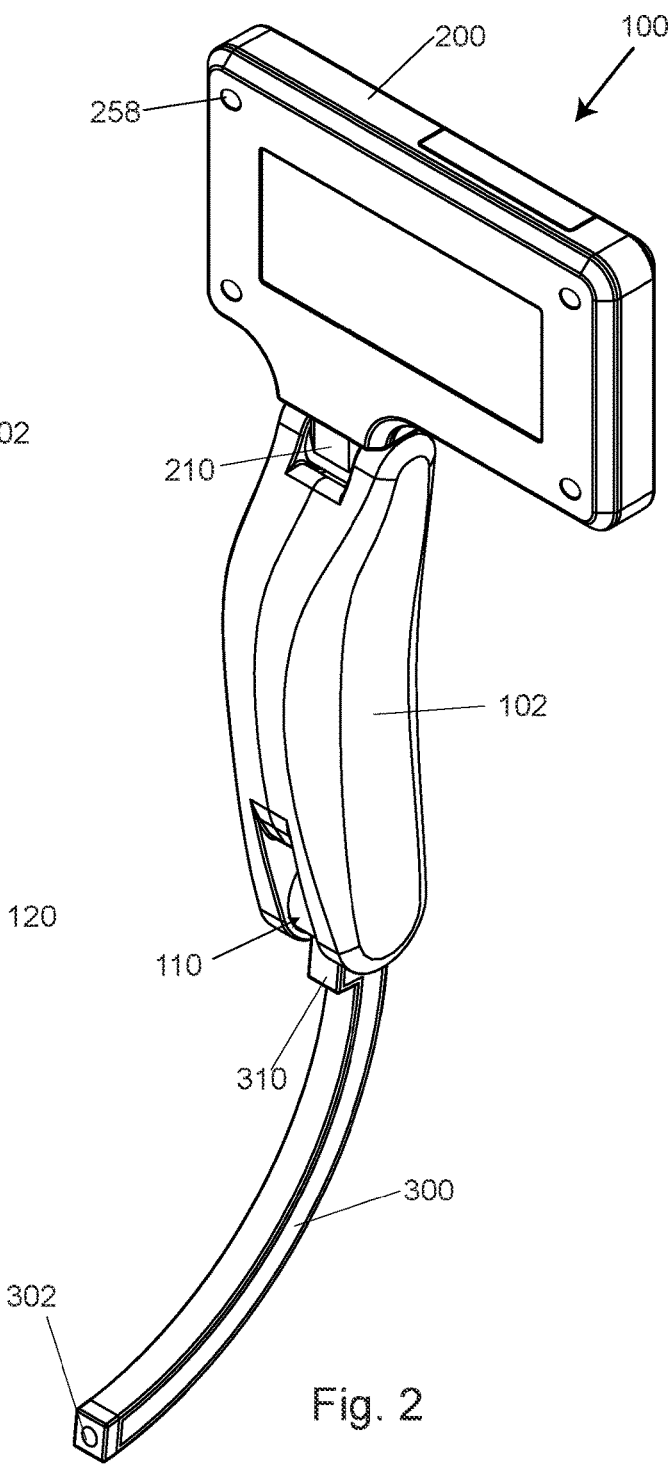
FIG. 2 is a diagram of another perspective view of an example video laryngoscope with a handgrip, a communication unit, and a camera arm unit for retaining a laryngoscope blade, according to embodiments of the present disclosure.
Figure 3:
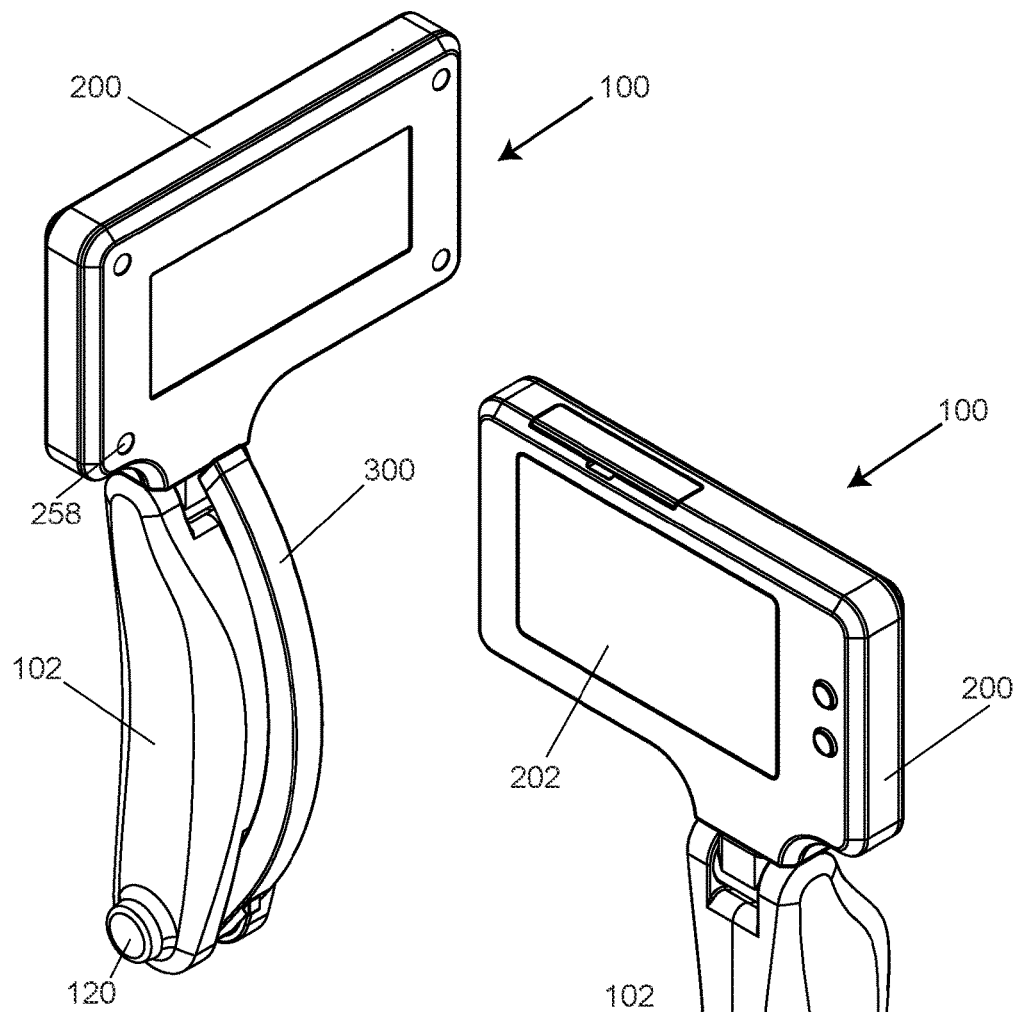
FIG. 3 is a diagram of a perspective view of an example video laryngoscope showing the camera arm folded alongside the handgrip, according to embodiments of the present disclosure.
Figure 4:
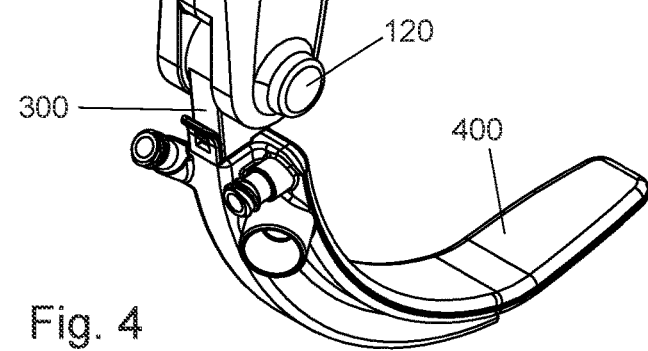
FIG. 4 is a diagram of a perspective view of an example video laryngoscope showing the camera arm with a laryngoscope blade attached thereto, according to embodiments of the present disclosure.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

FIGS. 1-4 show perspective views of an example laryngoscope 100, according to embodiments of the present disclosure. The laryngoscope 100 may include an elongated apparatus body 102 shaped for holding by one hand. In some embodiments, the apparatus body 102 may be referred to herein as body 102 or a handgrip 102. In some embodiments, body 102 may include an opening that allows for a user to easily grip and hold the laryngoscope 100 in one hand. At a proximal end (e.g., upper end) of the body 102, the laryngoscope 100 includes a communication unit 200 with a screen 202, connected to a linkage 210 for positioning at different angles relative to the body or handgrip 102. In some embodiments, the linkage 210 has a sealed two-axis configuration, in which the linkage 210 may allow for rotation or adjustment of the communication unit 200 with respect to the body 102 along a vertical and a horizontal axis. A laryngoscope camera arm unit 300 (e.g., a blade arm) with associated laryngoscope blade 400 attached thereto is mounted utilizing a rotary position linkage member 110 to a distal end (e.g., lower end) of body 102. The rotary position linkage member 110 may allow folding of the camera arm 300 along the body 102 and also positioning of the camera arm 300 at different angular positions outwards relative to the body 102. In some embodiments, the rotary position linkage member 110 may be referred to herein as a linkage or position linkage member. In some embodiments, the camera arm 300 may be kept fixed in any selectable position by releasing a lock button 120, which may be located on a side of the distal end of body 102.

Figure 5:
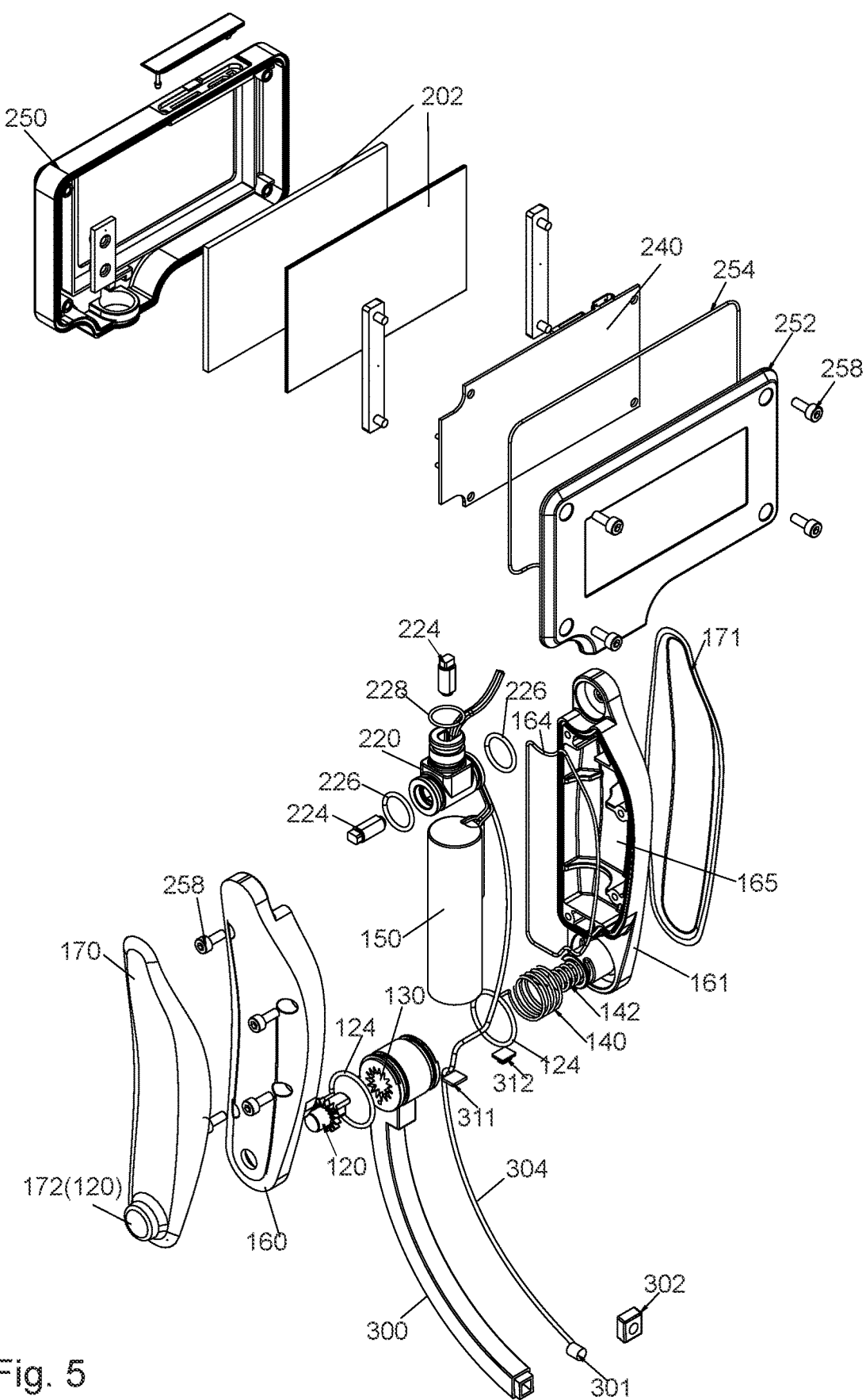
FIG. 5 is a diagram showing an exploded view of the laryngoscope apparatus as shown in FIGS. 1-3, according to embodiments of the present disclosure.
Figure 6:
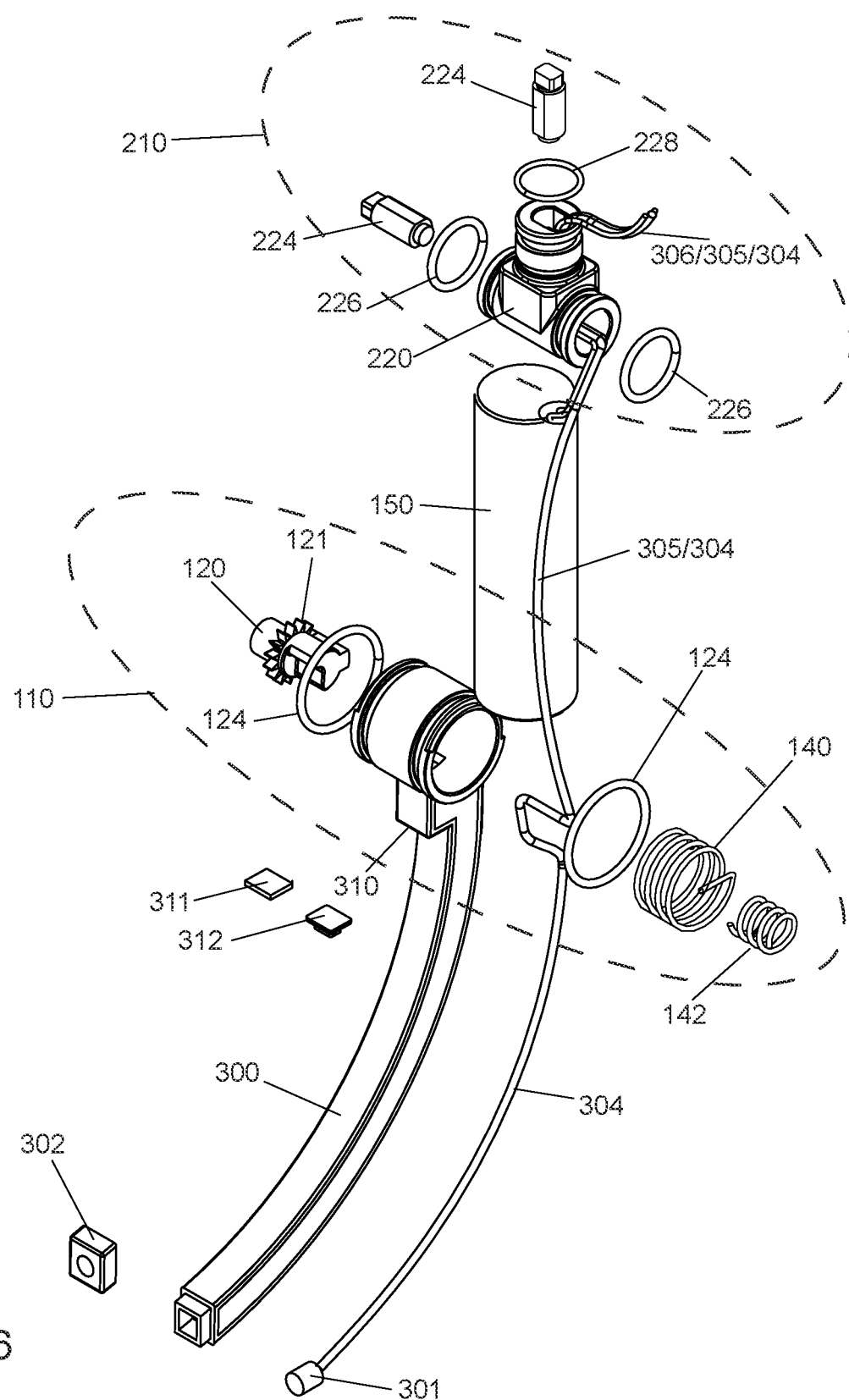
FIG. 6 is a diagram showing an exploded view of an example linkage device between a communication unit and a handgrip, and a position linkage member between the handgrip and the camera arm, according to embodiments of the present disclosure.

The camera arm 300 (blade arm) may include a camera 301 and lens 302 at its distal position and a light source 310, LED 311, with window 312 located at the proximal end, closer to the linkage 110. Camera 301, LED 311, and window 312 are shown in FIGS. 5 and 6, which show exploded views of the laryngoscope apparatus and linkage device, respectively, according to embodiments of the present disclosure.

The camera arm 300 is shaped to retain a laryngoscope blade 400 with a channel 410 that is specially designed to be fitted onto the camera arm 300 (as shown in FIGS. 18 and 21-23). In some embodiments, the channel 410 may have a tubular shape. In some embodiments, the channel 410 may be referred to herein as a tubular portion, a slot, and/or a blade channel. In addition to the channel 410 of the blade 400, the blade 400 may include another portion comprising a main body 400' (shown in FIG. 21) and an outer lid or blade surface portion 402.

In some embodiments, light produced (e.g., by light source 310 and/or LED 311) may be transported through the blade 400 when the blade 400 is made of a light-emitting material to enhance illumination of an oral cavity of a patient. To increase the transmission of light into the blade 400, several LED units 314 may be located along the camera arm as illustrated in FIG. 7. In alternative embodiments, the blade 400 might not be made of a light-emitting material, and a light source 310' may be placed in close proximity to the camera at a distal end of the camera arm 300, as illustrated in FIG. 7. In such cases, the dimensions of camera arm 300 and channel 410 of the blade 400 may be increased to fit the light source 310'.

Figures 17, 18:
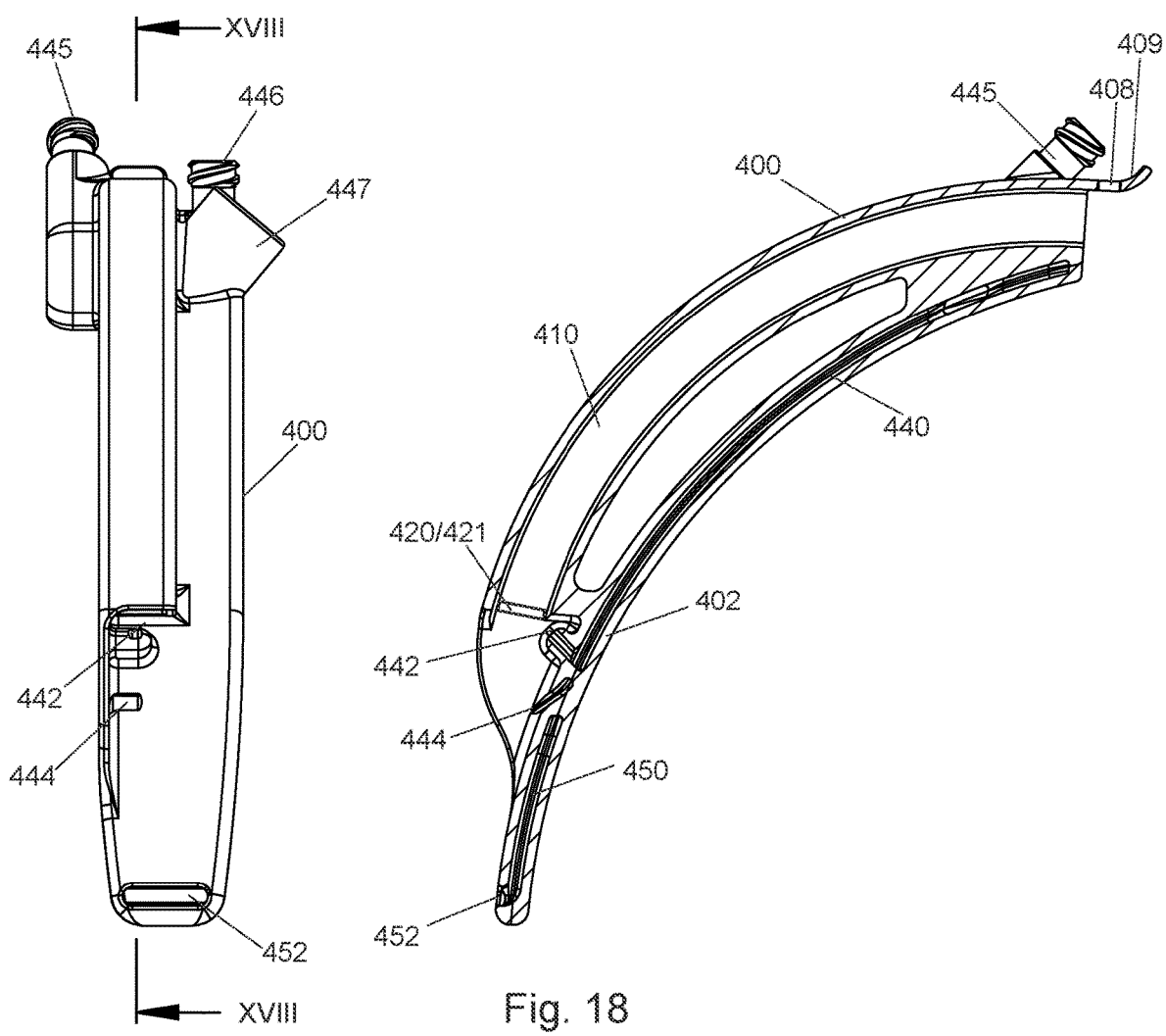
FIG. 17 is a diagram showing a view of an example laryngoscope blade, according to embodiments of the present disclosure.
FIG. 18 is a diagram showing section XVIII of the laryngoscope blade of FIG. 17, according to embodiments of the present disclosure.

In some embodiments, the body of the blade 400 may be made of a light-emitting material, except for an area of the blade 400 in front of the camera 301, which may include a transparent window 420 or lens 420 in the blade 400 (shown in FIGS. 15, 16, and 18). As the blade 400 is illuminated by the light source 310, the oral cavity of the patient may be illuminated for view and image capture by the camera 301. In some embodiments, the camera 301 and associated image processing may be equipped with means for measuring anatomical geometrics of the throat cavity.

In some embodiments, the apparatus body 102 may be shaped for easy grip by one hand and may include a release and lock button 120 configured to control angular positioning of the camera arm 300 and the blade 400 by provision of the position linkage member 110. In some embodiments, the release and lock button 120 may be accessible for operation by a user using one finger on the hand holding the body 102, or any finger of the other hand of the user. In some embodiments, the release and lock button 120 may be referred to herein as a push button and/or a lock button. When a user pushes down on the lock button 120, the position linkage member 110 may be assist the user in finding a proper and suitable angle for the operation of the blade 400 and may releasably hold the camera arm 300 fixed in an angular position relative to the apparatus body 102 by releasing the lock button 120.

Figure 9:
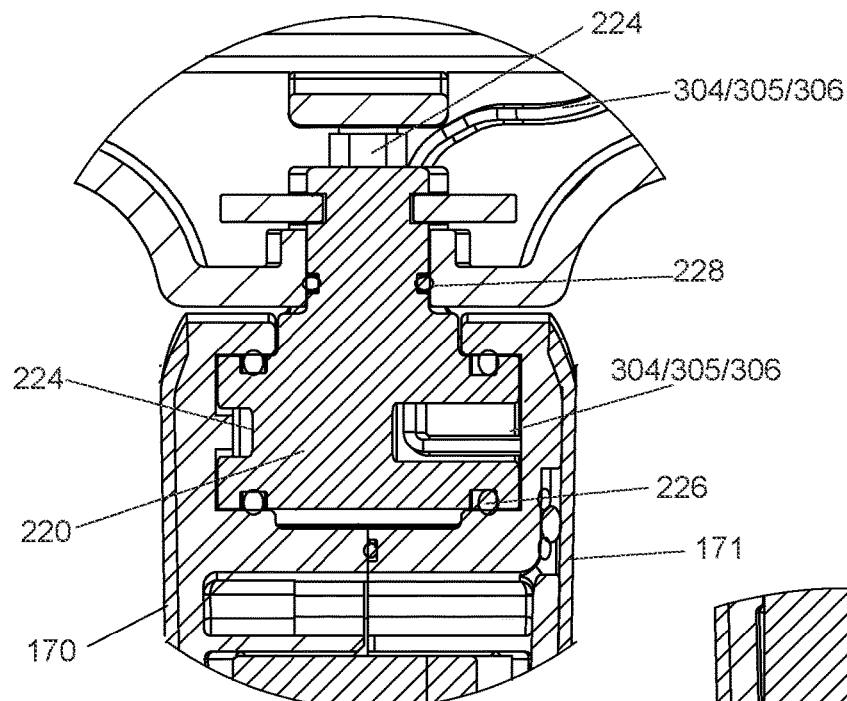
FIG. 9 is a diagram showing an enlarged view of section IX of the laryngoscope from FIG. 8, according to embodiments of the present disclosure.
Figure 10:
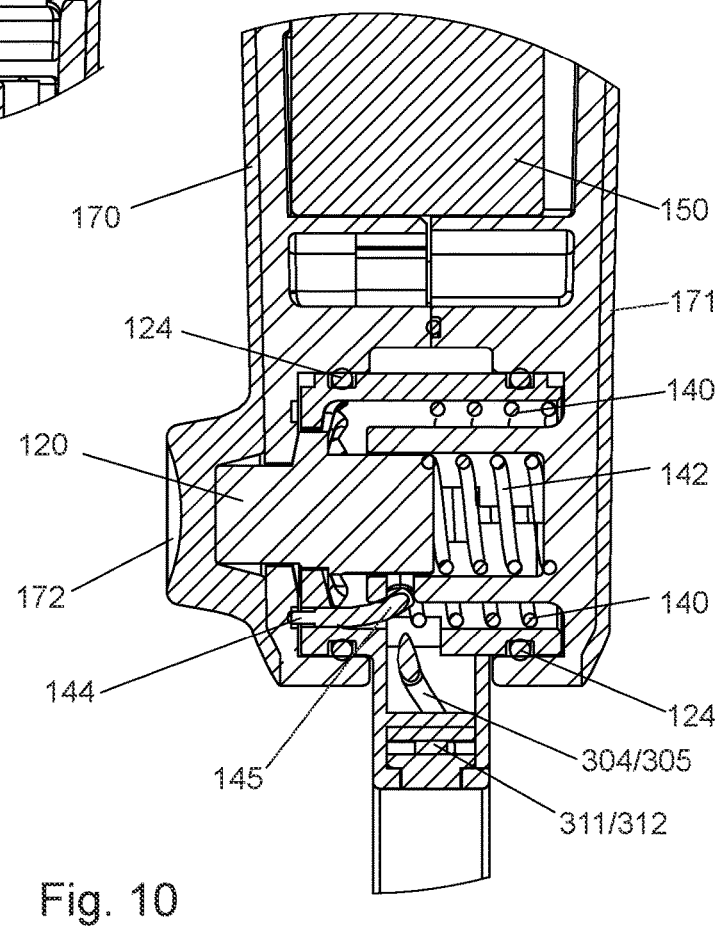
FIG. 10 is a diagram showing an enlarged view of section X of the laryngoscope from FIG. 8, according to embodiments of the present disclosure.
Figure 13:
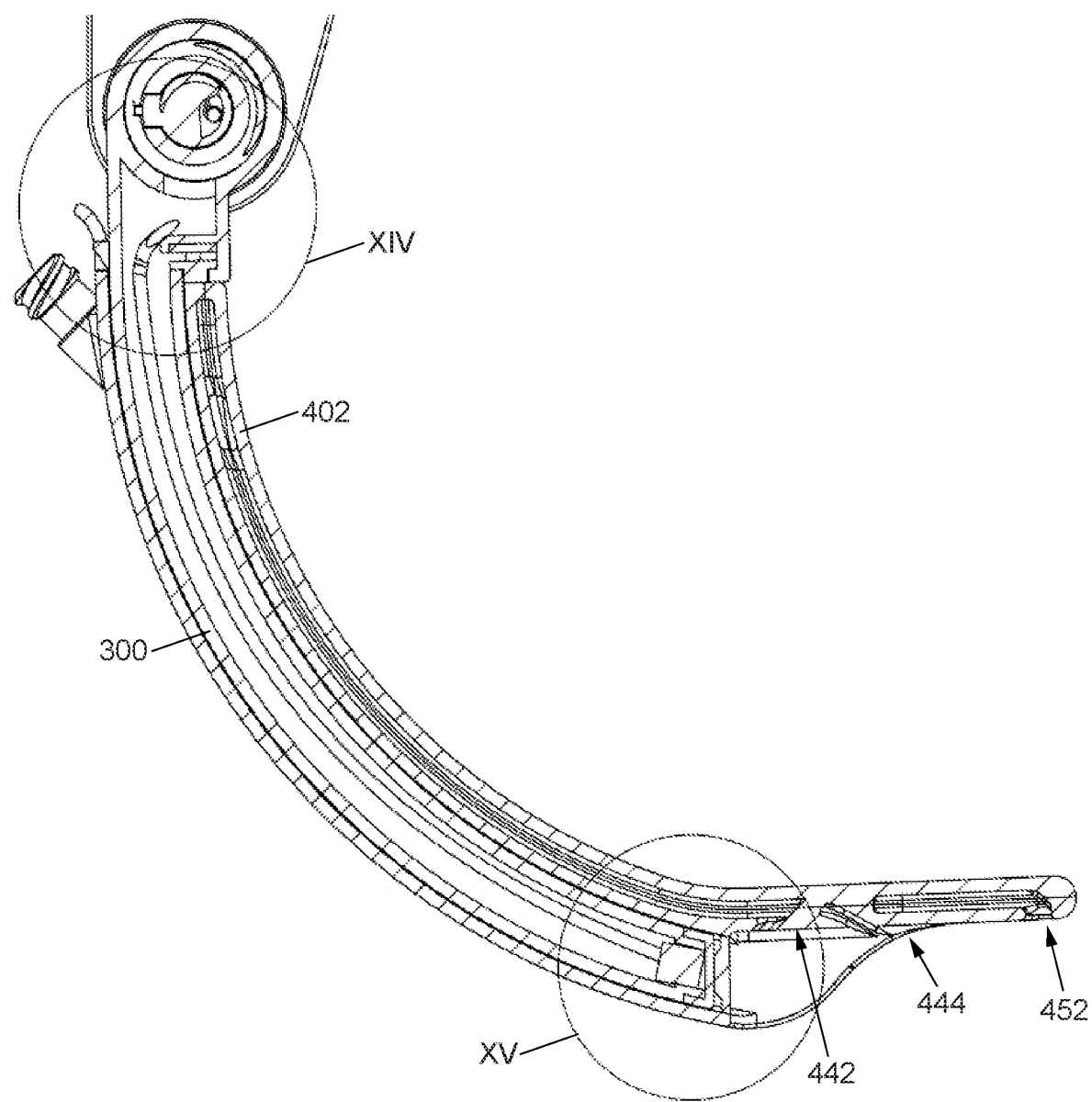
FIG. 13 is a diagram illustrating an example interaction between the camera arm and the blade of the laryngoscope, according to embodiments of the present disclosure.

Exploded views of the video laryngoscope apparatus and the linkage devices are shown in FIGS. 5 and 6, respectively, and sections of details in FIGS. 8-10 support the following description of the linkage device 210 of the communication unit 200 and the camera arm 300 of the position linkage member 110.

In some embodiments, rotary position linkage member 110 connecting the camera arm 300 to the apparatus body or handgrip 102, is a spring and clutch assembly comprising of: lock button 120 fixed with a toothed collar 121 that engages in a circular toothed portion 130 at the proximal end of camera arm 300. Torsion spring 140 is connected with the camera arm 300 and body 102, employing a force on the camera arm 300 in the direction towards the body 102 into a folded position. A compression spring 142 engages with lock button 120 with the tension keeping toothed collar 121 in engagement with the circular toothed portion 130 and locking the camera arm 300 from movement. Push movement of the lock button 120 releases the toothed portions from engagement and enables the movement of the camera arm 300, and if not stopped by the user, the camera arm 300 will return to the folded position.

With further reference to FIGS. 5 and 6, the linkage 210 for connecting the communication unit 200 with the body or handgrip 102, may comprise a pivot unit 220 with protrusions in two directions where friction hinges 224 are fixed. In some embodiments, the protrusions may be configured to allow signal and power cables 304, 305, 306 to pass through pivot unit 220 and linkage 110, providing for power from a power source 150 (e.g., a battery) to one or more components and for signals between camera 301, light source 310, and one or more sensors to the communication unit 200. In some embodiments, a cable solely for the camera 301 is denoted 304, and cables for camera 301, light source 310, and one or more sensors are denoted 305/306. In some embodiments, one or more functions to the communication unit, CPU, and O-rings for sealing the linkages have numerals 124, 226 and 228, respectively.

FIG. 5 also shows housing parts 160, 161 of the body 102, with the power source 150 centrally placed. Gasket 164 seals the battery compartment 165. The body 102 has rubber covers 170, 171 on two sides of the body 102. Cover 170 has a portion 172 for covering the lock button 120 and also permitting a pressing function onto the lock button 120. The communication unit as shown in FIG. 5 comprises a printed circuit board (PCB) and computer unit 240 and display and screen 202. The housing of the communication unit 200 comprises two parts 250, 252 with gasket 254 and screws 258 for sealing the parts together. In additional and/or alternative embodiments, the housing and/or casing of the laryngoscope may be secured and sealed by welding or by adhesives. In some embodiments, the laryngoscope housing and/or casing may be secured by welding and/or by adhesives to provide a sealed product and also to prevent unauthorized opening of the housing.

In some embodiments, the laryngoscope may have means for measuring force used on the camera arm 300 and angle detection of the position of the camera arm 300. In some embodiments, the means for measuring force may include one or more sensors, such as an angle and force sensor and/or an angular torsion sensor. FIG. 10 shows an angle and force sensor 144. In some embodiments, sensor 144 may be connected with a portion of body housing 160 and may detect a change in rotation of the camera arm 300. A sensor 145 may also be connected with torsion spring 140 or between the rotating parts for measuring its tension. The sensor 145 may be a force-torque sensor. FIGS. 9 and 10 also show details as described with reference to FIGS. 5 and 6.

FIGS. 11 and 12 show the laryngoscope with a blade 400 fixed onto camera arm 300, according to embodiments of the present disclosure. Detail section XIV on FIG. 12 is shown in an enlarged view in FIG. 14 and shows light source 310 comprised of LED 311 and window 312. In some embodiments, the blade 400 is made of a light-emitting material that is illuminated by LED, and an oral cavity of a patient is thereby illuminated for view and image capture by the camera 301. As shown in FIG. 15, the window in front of the camera may comprise a lens 421 fixed in the blade 400. Thereby, a lens 302 for the camera 301 (shown in FIG. 5) may be redundant and replaced by a transparent window 303. FIG. 16 shows the camera 301 located at the distal end of the camera arm 300, behind a lens 302 fixed to the camera arm 300. In embodiments where the blade 400 is made of a light-emitting material and not transparent, a transparent window 420 is fixed within the blade 400 in front of the camera 301, thereby allowing an uninhibited view for imaging. In some embodiments, the transparent window 420 may prevent contamination of the camera 301 and the lens 302 attached to the arm 300.

Figures 19, 20:
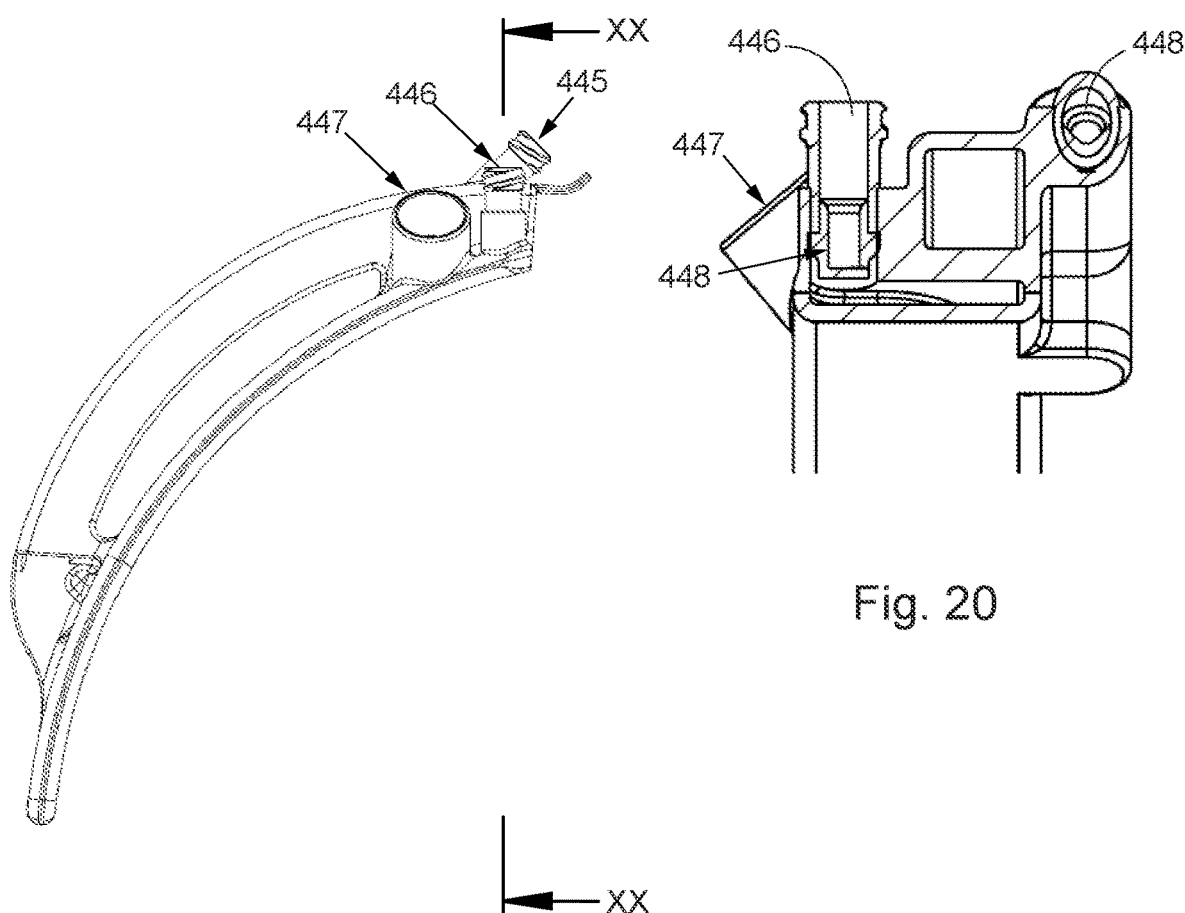
FIG. 19 is a diagram showing a partial sectional view of the laryngoscope blade, according to embodiments of the present disclosure.
FIG. 20 is a diagram showing section XX of the laryngoscope blade of FIG. 19, according to embodiments of the present disclosure.
Figure 21:
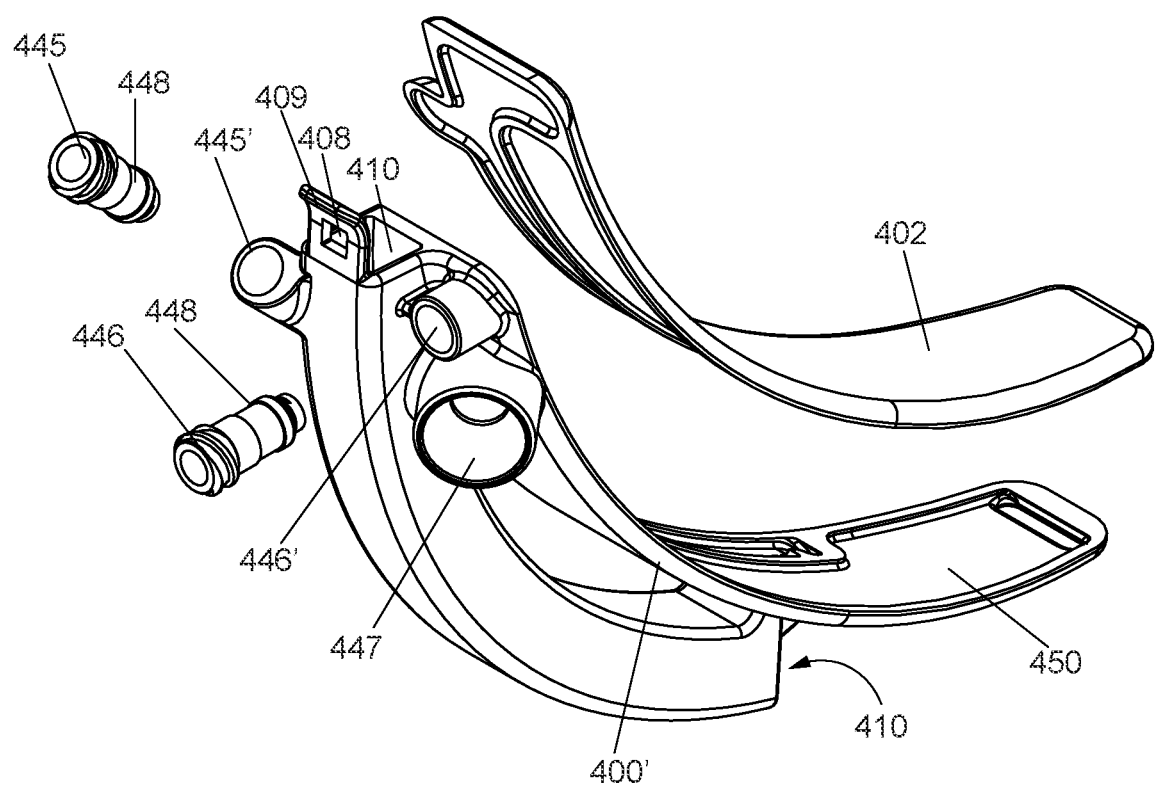
FIG. 21 is a diagram showing an exploded view of an example laryngoscope blade, according to embodiments of the present disclosure.
Figure 22:
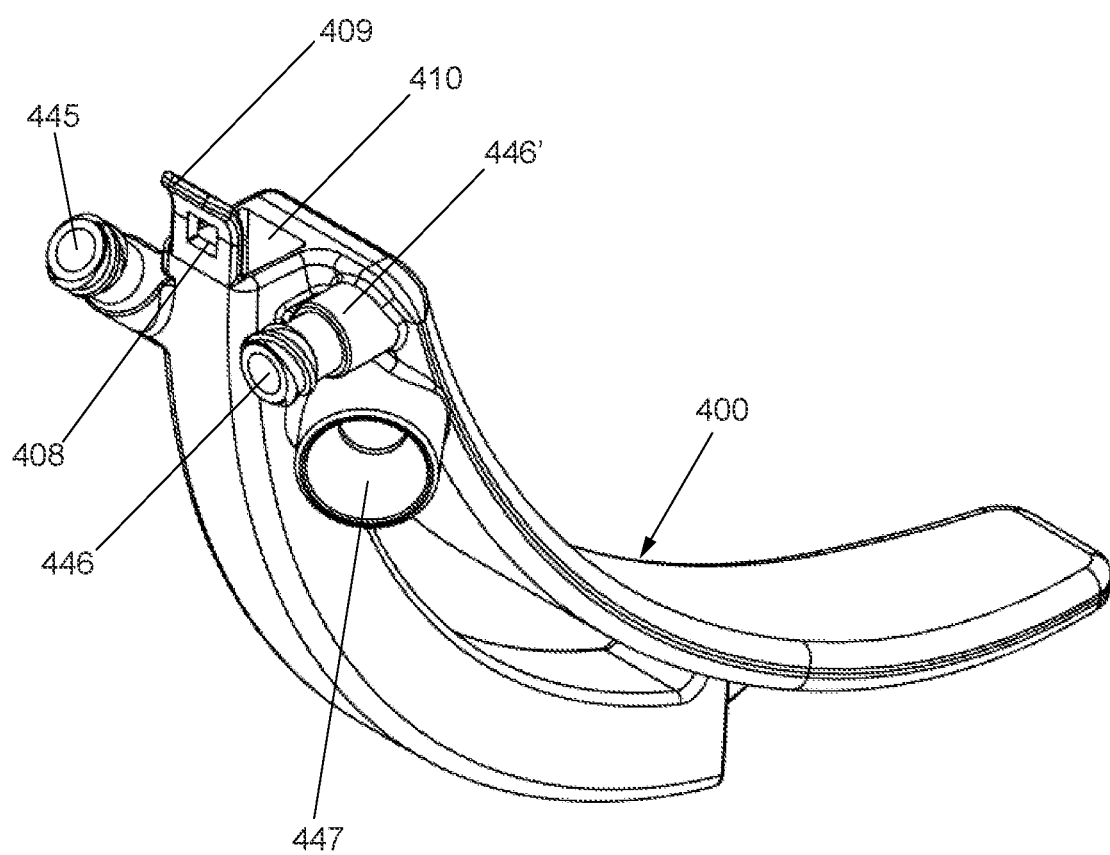
FIG. 22 is a diagram showing an example laryngoscope blade in an assembled state, according to embodiments of the present disclosure.

With the support of FIGS. 17, 18, 21 and 23, as well as FIGS. 19, 20 and 22, the laryngoscope blade 400 will be further described. As described above, the blade 400 has a channel or slot 410 where camera arm 300 is inserted. The laryngoscope may be equipped with blades of different shapes and sizes. In some embodiments, the curvature of the camera arm 300 might not need to be the same as the curvature of the outer lid or blade surface portion 402, which is the case of the embodiment shown in FIG. 12. FIG. 18 shows that the curvature of the outer lid or blade surface portion 402 is less than the curvature of the camera arm 300 and thereby the blade channel 410. In some embodiments, the outer lid or blade surface portion 402 of the blade 400 has a selectable range of radius of curvature.

Figure 23:
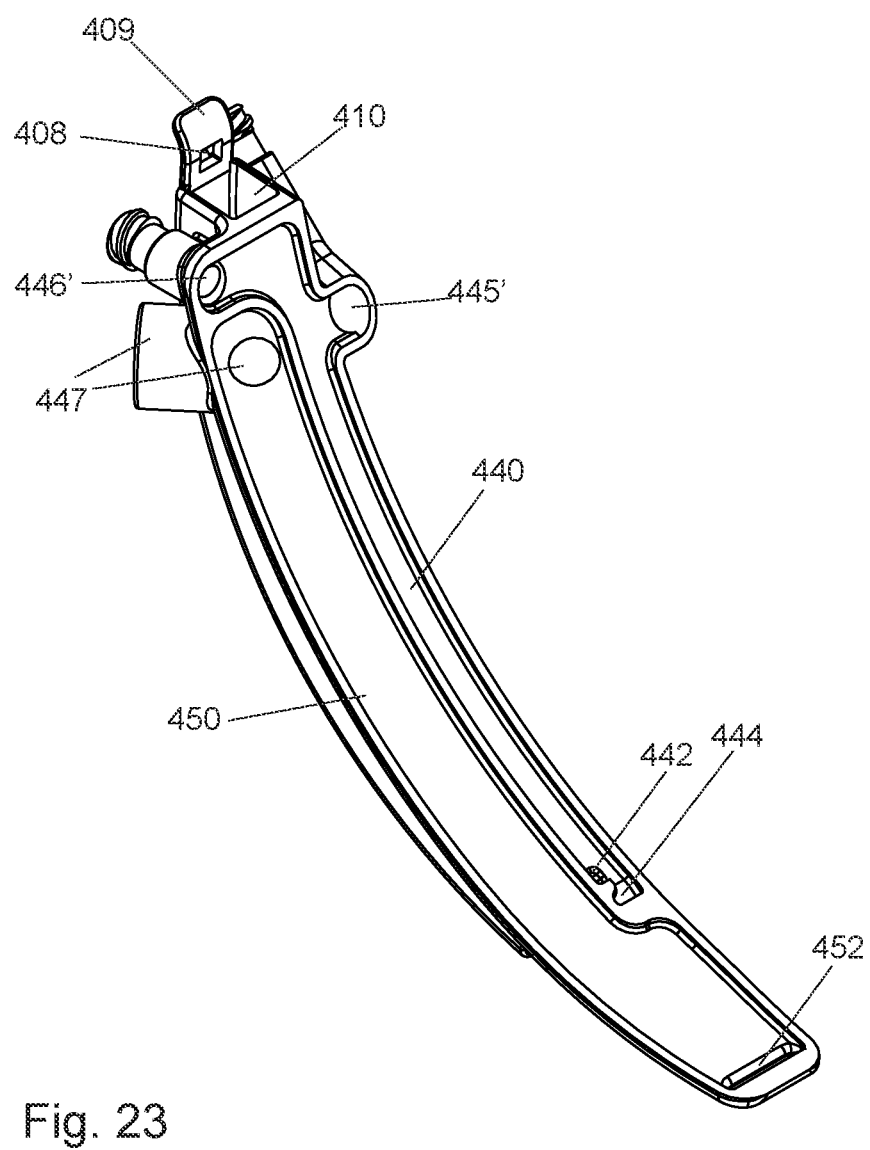
FIG. 23 is a diagram showing an inside view of an example laryngoscope blade, according to embodiments of the present disclosure.

In some embodiments, the proximal end of the camera arm 300 may include a catch 308 as amongst others shown in FIGS. 1, 7 and 14. In some embodiments, the catch 308 may be a fastener. The catch 308 may engage in a slot 408 (shown in FIGS. 18 and 21-23) on a flexible tongue 409 at the proximal end of the blade 400. In some embodiments, the slot 408 may be referred to as an arresting device that is configured to releasably engage with the catch 308 on the proximal end of the camera arm 300. In some embodiments, the blade 400 may include enclosed channels 440 for fluid transport of gas, such as oxygen, local anesthetics, and fluid for cleansing of the camera lens 421 or the transparent window 420, with a separate enclosed channel 450 for suction of bodily fluids from the patient, e.g. saliva, blood and/or vomit, although these examples are non-limiting. FIG. 23 further shows opening 442 for cleansing of lens window, opening 444 for gas, oxygen, and/or local anesthetics, opening 452 at the distal end of the blade 400 for suction of fluids. In some embodiments, the cleansing of the lens window may be related to a removal of any debris or obstacles blocking a clear view for the camera. The proximal end of the blade 400 may include openings 445', 446' for connectors 445, 446 on the blade for the tubes for transporting fluids (e.g. gas) and opening 447 for suction. Fluid connectors 445, 446 for e.g. gas and anesthetics may be of Luer type and may also be equipped with check valves 448. Opening 447 may be for suction of bodily fluids such as saliva, blood or vomit. As shown in FIGS. 21 and 23, the two fluidic channels 440 and 450 exhibit mutually different cross-sectional areas along a majority of their lengths. The fluidic channel 450 exhibits the largest cross-sectional area and is the patient fluid suction channel.

In some embodiments, the video laryngoscope apparatus includes several sensors and functions that provide feedback to the user. For example, sensor 145 may detect the level of force used on the blade on the patient, which may be shown on the screen 202 and/or by light indicators or sound. In some embodiments, a warning signal or sound may be included in the communication unit if the level of force is of danger to a patient. An additional or alternative embodiment may include a unit for vibration 270 (shown in FIG. 24), which may be activated to provide a vibration notification or feedback to the user in cases where sound or visual information is difficult for the user to detect. In some embodiments, angles of the camera arm may be detected by sensor 144 and may be visualized on the screen 202.

In some embodiments, the feedback features of the laryngoscope apparatus, such as measuring force, angles, anatomical geometries, images, and other related medical information that is directed to the user as a consequence of the operation of the laryngoscope, may be recorded locally on the communication unit and/or on a secure remote database for later analysis and later studies of the intubation operation together with records of images and other operations during the time of usage of the laryngoscope.

In some embodiments, information and images may be shown on a screen or display of the communication unit 200 or any other connected computer unit screen. In some embodiments, the laryngoscope communication unit may be voice-operated or by touch screen, and/or by key function buttons. In some embodiments, the laryngoscope communication unit may include means for remote communication and sharing of data with other resources, such as databases (e.g., medical databases, electronic medical record (EMR) systems, or the like), or other specialized personnel located remote from the site of operation. In some embodiments, the laryngoscope communication unit may comprise a memory and a processor configured to securely store and transmit data obtained during usage of the laryngoscope on a patient, respectively. In some embodiments, the data may comprise at least one of measured force, measured angles, software images, video, and other related medical information obtained during laryngoscopy.

Figure 24:
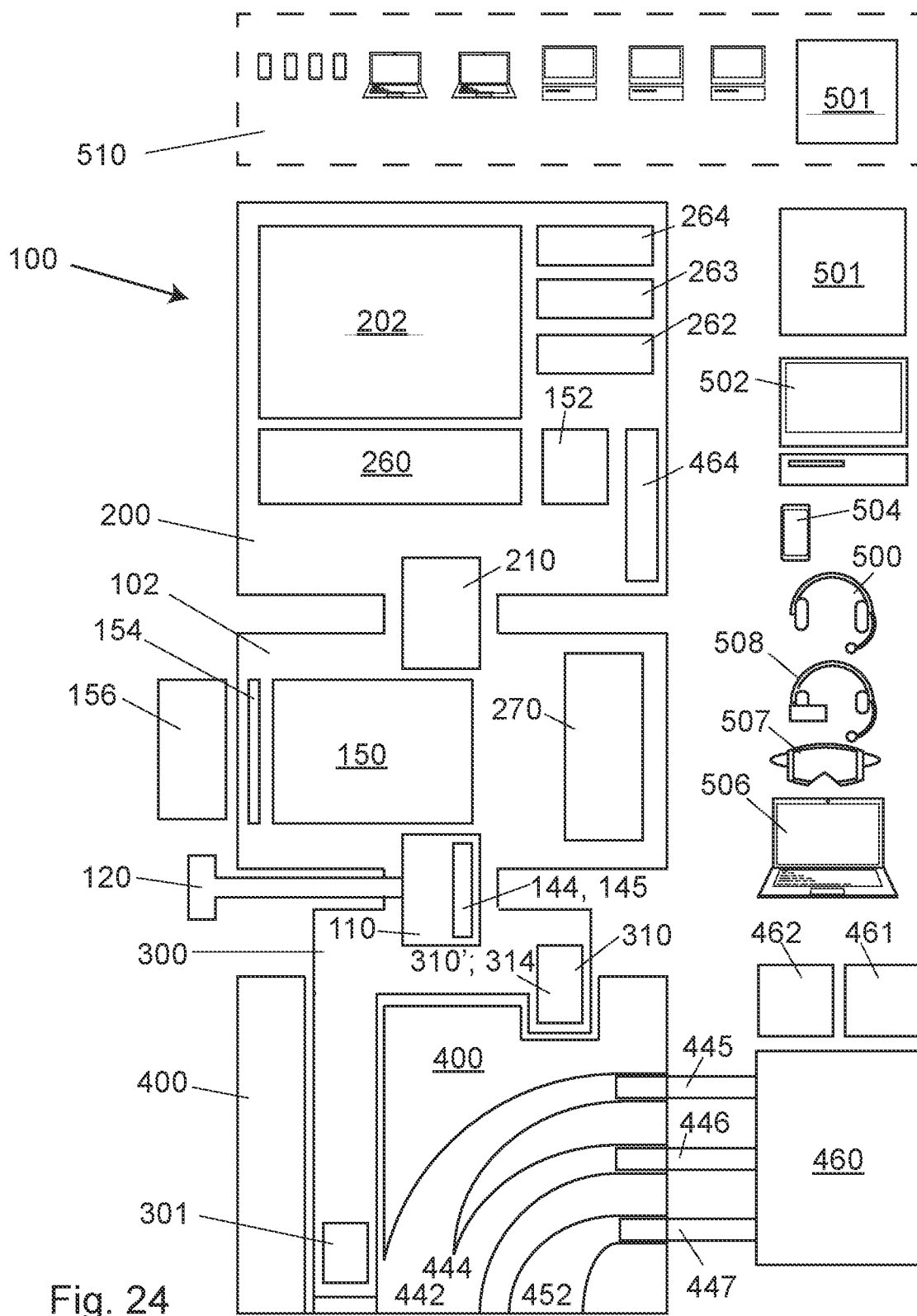
FIG. 24 is a schematic diagram of an example laryngoscope and how operational parts are interrelated in the laryngoscope, according to embodiments of the present disclosure.

FIG. 24 is a schematic diagram of the laryngoscope 100, according to embodiments of the present disclosure. The laryngoscope 100 is shown with body 102, communication unit 200, camera arm 300, and blade 400. In some embodiments, power from power source 150 to the functional elements, such as light source and communication unit, is transmitted using one or more cable leads through linkages 210 and 110. In some embodiments, the casing of the laryngoscope is sealed by welding or adhesives, and the power source is solely accessible by authorized personnel at a service. In such embodiments, charging by induction may be included, as illustrated by numeral 154 and 156.

The power controller 152 controls and distributes power to the computer processing unit (CPU) 260 of the communication unit 200, which in turn is connected through cables to provide power and receive signals from the camera 301, power the light source 310, 310', 314, and power and receive signals from the sensors 144, the cables passing through the linkages 110, 210. The communication unit 200 and CPU 260 with a processor and local storage may have means for connecting to other resources, such as wirelessly through WIFI, radio and/or wireless phone systems, represented by ports 262, 263, and 264. In some embodiments, the communication unit 200 may include a communication interface configured to connect to other resources/devices and securely transmit and receive data to and from the other resources/devices.

In some embodiments, the communication unit 200 may be any modern computer or smartphone type available on the market. A feature of the disclosure is that the communication unit may transmit data and communicate audio/video with other resources, for example, in a WebRTC (Web Real-Time Communication) configuration, which is an open-source system that provides web browsers and mobile applications with real-time communication via simple application programming interfaces (APIs).

In some embodiments, FIG. 24 further illustrates the control of supplying anesthetics, cleansing fluids and oxygen and/or suction by the control unit 460 during use of the laryngoscope. In some embodiments, the supply of fluid and/or gas may either be manually controlled 461, or controlled by automated means 462 by use of communication unit with touch screen or voice-control. Additionally or alternatively, special buttons 464 located on the video laryngoscope body 102 or the communication unit 200 may be used. The video laryngoscope may connect with remote equipment such as an audio headset 500, VR 507 (Virtual Reality Goggles) and/or any head-mounted visual display 508 close to at least one eye of an operator, all of which may be advantageous when using a voice control system. The headset 500, and/or any of said remote equipment may be locally connected to laryngoscope 100 by wired or wireless system(s), or to a remote computer 502 with wireless connection while also connected with the laryngoscope 100. The laryngoscope 100 may also be connected to a server 501, which serves as a connection point for several resources such as computers 502, smartphone 504, or PC 506. In some embodiments, the laryngoscope may be configured through a WebRTC system to communicate with remote resources 510 (e.g., servers and computer units) and share data with other resources, such as databases (medical), or other special personnel remote from the site of operation.

Thereby, the laryngoscope may be remotely guided or operated by personnel performing intubation on a patient through communication through video images, commands, and information on-screen and audio communication, especially where a headset is connected.

The present disclosure described can be subject to modifications and variations without thereby departing from the scope of the concept as disclosed with reference to the drawings and further stated in the claims. To the extent that certain functional elements can be replaced by other elements to enable the same function to be performed by the various embodiments disclosed, such technical equivalents are included within the scope of the disclosure.

Exemplary Computing Embodiments

Figure 25:
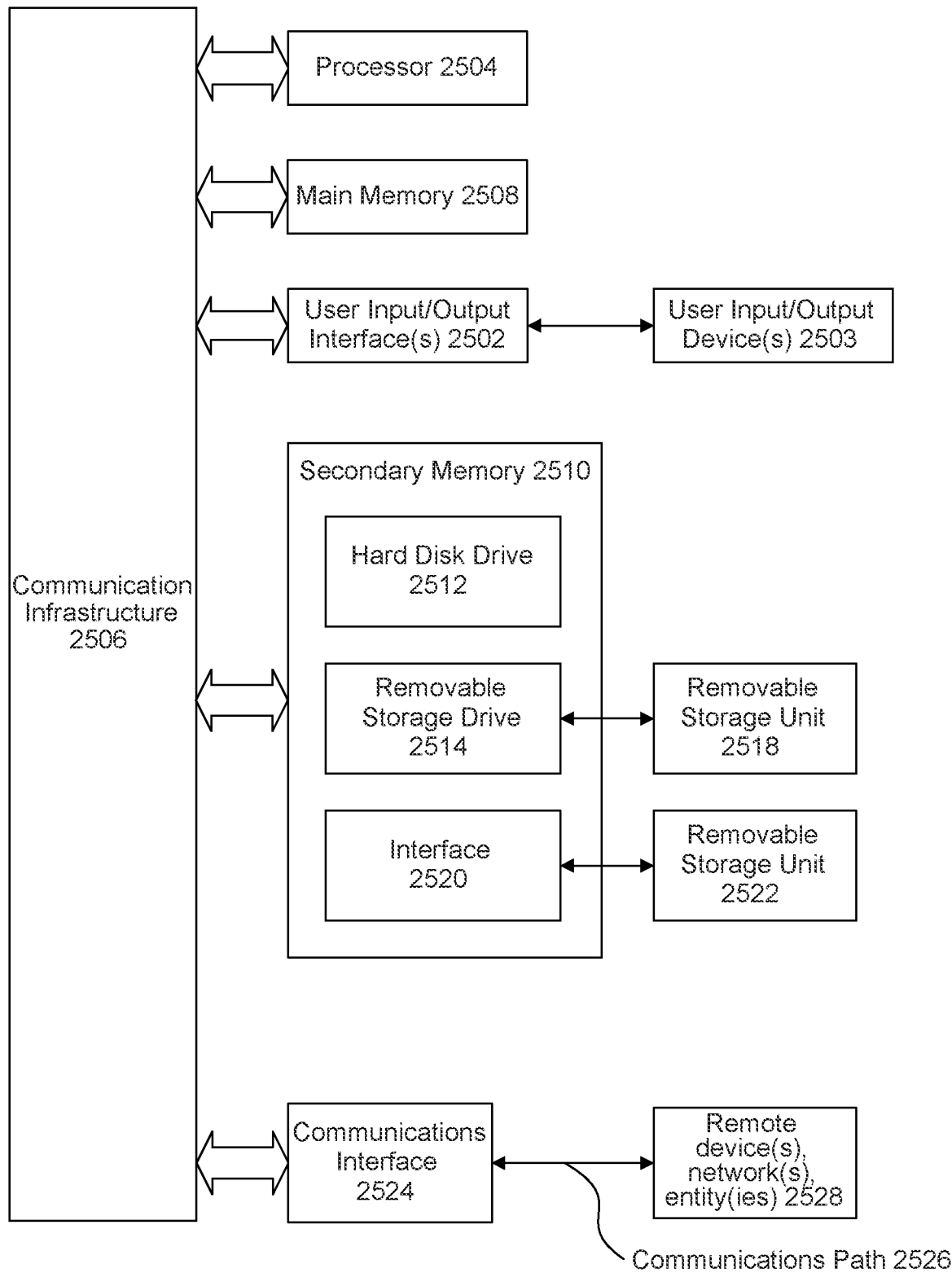
FIG. 25 illustrates a block diagram of example components of a computer system, according to embodiments of the present disclosure.

FIG. 25 is a block diagram of example components of computer system 2500. One or more computer systems 2500 may be used, for example, to implement any of the embodiments discussed herein, as well as combinations and subcombinations thereof. In some embodiments, one or more computer systems 2500 may be used to implement the methods, computing, and processing devices, as described herein. Computer system 2500 may include one or more processors (also called central processing units, or CPUs), such as a processor 2504. Processor 2504 may be connected to a communication infrastructure or bus 2506.

Computer system 2500 may also include user input/output interface(s) 2502, such as monitors, keyboards, pointing devices, etc., which may communicate with communication infrastructure 2506 through user input/output interface(s) 2503.

One or more of processors 2504 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 2500 may also include a main or primary memory 2508, such as random access memory (RAM). Main memory 2508 may include one or more levels of cache. Main memory 2508 may have stored therein control logic (i.e., computer software) and/or data. In some embodiments, main memory 2508 may include optical logic configured to perform processing and analysis of observations made by the camera on the camera arm of the video laryngoscope apparatus.

Computer system 2500 may also include one or more secondary storage devices or memory 2510. Secondary memory 2510 may include, for example, a hard disk drive 2512 and/or a removable storage drive 2514.

Removable storage drive 2514 may interact with a removable storage unit 2518. Removable storage unit 2518 may include a computer usable or readable storage device having stored thereon computer software (control logic) and/or data. Removable storage unit 2518 may be a program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 2514 may read from and/or write to removable storage unit 2518.

Secondary memory 2510 may include other means, devices, components, instrumentalities or other approaches for allowing computer programs and/or other instructions and/or data to be accessed by computer system 2500. Such means, devices, components, instrumentalities or other approaches may include, for example, a removable storage unit 2522 and an interface 2520. Examples of the removable storage unit 2522 and the interface 2520 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 2500 may further include a communication or network interface 2524. Communication interface 2524 may enable computer system 2500 to communicate and interact with any combination of external devices, external networks, external entities, etc. (individually and collectively referenced by reference number 2528). For example, communication interface 2524 may allow computer system 2500 to communicate with external or remote devices 2528 over communications path 2526, which may be wired and/or wireless (or a combination thereof), and which may include any combination of LANs, WANs, the Internet, etc. Control logic and/or data may be transmitted to and from computer system 2500 via communication path 2526. In some embodiments, computer system 2500 may be coupled to input/output devices such as one or more of: the video laryngoscope camera, fluid control valves for fluid inlet into and through the interior of the laryngoscope blade, suction pump control for a pump linked to the outlet from the suction channel in the laryngoscope blade, the illumination LEDs to control brightness and/or intensity therefrom, the linkage sensors located at the posterior end of the camera arm interacting with the apparatus handgrip, other sensors, or operating devices, visual display, touch-screen, light signals, microphone, loudspeaker, headset, and intercom transceiver. In some embodiments, such coupling to and/or from the video laryngoscope and any components therein may be caused or effected by suitable connections via user input/output interface(s) 2502, and via a communications interface 2524 and communications path 2526 in the computer system 2500 for any required input/output communication with one or more remote devices, networks, and/or entities 2528.

Computer system 2500 may also be any of a personal digital assistant (PDA), desktop workstation, laptop or notebook computer, netbook, tablet, smartphone, smartwatch or other wearables, appliance, part of the Internet-of-Things, and/or embedded system, to name a few non-limiting examples, or any combination thereof.

Computer system 2500 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 2500 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 2500, main memory 2508, secondary memory 2510, and removable storage units 2518 and 2522, as well as tangible articles of manufacture embodying any combination of the foregoing. Such control logic, when executed by one or more data processing devices (such as computer system 2500), may cause such data processing devices to operate as described herein.

CONCLUSION

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A video laryngoscope apparatus for inspection of an oral cavity region of a patient, the video laryngoscope apparatus comprising:
   an apparatus body comprising a proximal end and a distal end, wherein the apparatus body is elongate and configured to be hand-held by an operator of the video laryngoscope apparatus;
   a camera arm comprising a proximal end and a distal end with a camera, wherein the proximal end of the camera arm is connected to the distal end of the apparatus body utilizing a rotary position linkage member that is adjustable, and wherein the camera arm is configured to receive and releasably attach thereto a disposable laryngoscope blade;
   a light source coupled to the camera arm;
   a communication device connected via a linkage device to the proximal end of the apparatus body; and
   a power source housed by the apparatus body,
   wherein the rotary position linkage member comprises:
      a torsion spring connected with the camera arm and the apparatus body inside the rotary position linkage member, wherein the torsion spring is configured to employ a force on the camera arm in a direction towards the apparatus body into a folded position; and
      a compression spring disposed inside the torsion spring, wherein the compression spring is configured to be engaged with a lock-release button, wherein the compression spring is configured to releasably lock the camera arm from moving by keeping first and second toothed units in engagement, and wherein the first toothed unit is disposed on the lock-release button and the second toothed unit is disposed on the camera arm.

2. The video laryngoscope apparatus of claim 1, wherein the rotary position linkage member comprises an angular torsion sensor.

3. The video laryngoscope apparatus of claim 2, wherein the angular torsion sensor is configured to detect a positional angle of the camera arm relative to the apparatus body and a torsional force applied to the camera arm, and transmit data signals to the communication device for feedback and process the data signals.

4. The video laryngoscope apparatus of claim 1, wherein the first toothed unit is a toothed collar fixedly attached to the lock-release button to releasably fit in and engage with the second toothed unit which is a circular toothed portion disposed on the proximal end of the camera arm.

5. The video laryngoscope apparatus of claim 4, wherein the torsion spring is configured to cause the camera arm to rotate and thereby guide the disposable laryngoscope blade towards the apparatus body when the lock-release button is pushed down upon.

6. The video laryngoscope apparatus of claim 4, wherein a release of operation of the lock-release button allows an angular positioning of the camera arm and the disposable laryngoscope blade fitted onto the camera arm for a return of the disposable laryngoscope blade towards a 90 degree angle position relative to the apparatus body or into a locked position of the camera arm.

7. The video laryngoscope of claim 4, wherein a toothed hole at the proximal end of the camera arm defines the circular toothed portion.

8. The video laryngoscope apparatus of claim 1, wherein the rotary position linkage member is sealed and has a wire lead-through passage for transmission of power and data for the light source and camera.

9. The video laryngoscope apparatus of claim 1, wherein the communication device comprises at least one of a computer unit, a touchscreen, or one or more connection ports for wired or wireless transmission of data.

10. The video laryngoscope apparatus of claim 1, wherein the linkage device has a sealed two-axis configuration.

11. The video laryngoscope apparatus of claim 1, wherein the communication device comprises a memory and a processor configured to store and transmit data, respectively.

12. The video laryngoscope apparatus of claim 1, wherein the communication device comprises a communication interface configured to transmit data wirelessly to other devices.

13. The video laryngoscope apparatus of claim 1, wherein the communication device includes a smartphone or a portable computer.

14. The video laryngoscope apparatus of claim 1, wherein the communication device is configured to connect and communicate with at least one of remote audio equipment or visual equipment.

15. The video laryngoscope apparatus of claim 1, wherein the power source is configured to power the communication device, the camera, the light source, and sensors related to at least one of angle, force, or force-torque in the rotary position linkage member, and wherein the power source is chargeable.

16. The video laryngoscope apparatus of claim 1, wherein the communication device is configured to process data related to signals from an angular torsion sensor in the rotary position linkage member, and wherein the communication device is further configured to provide feedback comprising at least one of video, images, audio, or physical force feedback to an operator of the video laryngoscope and any connected remote sources, the feedback being related to vital reactions of the patient and procedural methods for injury prevention.

17. The video laryngoscope apparatus of claim 1, wherein the communication device is configured to process data related to functions of the camera and sensor functions of sensors in an angular torsion sensor, and wherein the communication device is configured to provide feedback comprising at least one of video, images, or audio to at least one of the operator of the laryngoscope or any connected remote sources, the feedback being related to one or more of: vital reactions of the patient, observed conditions of the patient, stored records of the patient, and laboratory values.

18. The video laryngoscope apparatus of claim 1, wherein the communication device is configured to record data locally on at least one of the communication device or a secure remote database, wherein the secure remote database is associated with a patient record.

19. The video laryngoscope apparatus of claim 1, wherein the light source is located at one of: a) the proximal end of the camera arm, b) the distal end of the camera arm, or c) at multiple locations along the camera arm, wherein the disposable laryngoscope blade is illuminated by the light source, and wherein the disposable laryngoscope blade is made of a material configured to convey the light to an oral cavity of the patient.

20. The video laryngoscope apparatus of claim 1, wherein the disposable laryngoscope blade comprises a channel configured to releasably fit the disposable laryngoscope blade onto the camera arm.

21. The video laryngoscope apparatus of claim 20, wherein the channel is tubular.

22. The video laryngoscope apparatus of claim 20, wherein the channel, when enclosing the camera arm, is configured to seal the camera arm from contact with the patient and body fluids of the patient.

23. The video laryngoscope apparatus of claim 1, wherein the disposable laryngoscope blade has a first enclosed fluid channel for conveying fluid supply of at least one of gas, local anaesthetics, or cleaning fluid, and a second enclosed fluid channel for suction of excess fluids of the patient from an inlet opening.

24. The video laryngoscope apparatus of claim 23, wherein the first enclosed fluid channel comprises a first exit opening and a second exit opening, wherein the first exit opening is configured to deliver fluid towards a camera lens or a window for cleaning thereof.

25. The video laryngoscope apparatus of claim 24, wherein the first exit opening and the second exit opening are located, spaced apart, between a proximal end and a distal end of the disposable laryngoscope blade, and wherein the inlet opening is located at the distal end of the disposable laryngoscope blade.

26. The video laryngoscope apparatus of claim 1, wherein the disposable laryngoscope blade is removable.

27. The video laryngoscope apparatus of claim 1, wherein the communication device is configured to provide data of a position and a force of the disposable laryngoscope blade by at least one of an audio notification or a visual notification on a screen of the communication device or by a vibration notification.

* * * * *